United States Patent [19]

Shimizu et al.

[11] Patent Number: 4,761,508

[45] Date of Patent: Aug. 2, 1988

[54] 1,1-(3-ETHYLPHENYL)PHENYLETHYLENE AND METHOD FOR PREPARING IT

[75] Inventors: Isoo Shimizu; Yasuo Matsumura, both of Yokohama; Shigenobu Kawakami, Ichikawa; Atsushi Sato, Tokyo, all of Japan

[73] Assignee: Nippon Petrochemicals Co., LTD, Tokyo, Japan

[21] Appl. No.: 888,012

[22] Filed: Jul. 22, 1986

[30] Foreign Application Priority Data

Jul. 24, 1985 [JP] Japan ................... 60-163712

[51] Int. Cl.$^4$ .............................................. C07C 15/12
[52] U.S. Cl. ...................................... 585/25; 585/469
[58] Field of Search ............................... 585/25, 469

[56] References Cited

U.S. PATENT DOCUMENTS

| | | | |
|---|---|---|---|
| 3,898,288 | 8/1975 | d'Ostrowick et al. | 568/321 |
| 3,899,537 | 8/1975 | Holty | 568/321 |
| 3,965,185 | 6/1976 | Young | 568/321 |
| 4,086,277 | 8/1978 | Onopchenko et al. | 568/321 |
| 4,299,987 | 11/1981 | Dolhyj et al. | 568/321 |
| 4,493,943 | 1/1985 | Sato et al. | 585/11 |
| 4,543,207 | 9/1985 | Sato et al. | 585/436 |
| 4,568,793 | 2/1986 | Sato et al. | 585/25 |

FOREIGN PATENT DOCUMENTS

| | | |
|---|---|---|
| 52-8301 | 3/1977 | Japan . |
| 54-32459 | 3/1979 | Japan . |
| 51115452 | 10/1986 | Japan . |

OTHER PUBLICATIONS

Chem Abstract (1978) relates to Spanish Pat. No. 452500 (11/16/77).
Nametkin, N. S.; Synthesis of Alpha-Arylstyrenes *Neftekhimiya*, vol. 14(5), pp. 726–729 (1974).
Chem. Abstract 31038r, vol. 82, p. 475 (1975).

*Primary Examiner*—Curtis R. Davis
*Attorney, Agent, or Firm*—Fisher, Christen & Sabol

[57] ABSTRACT

The present invention is concerned with a novel intermediate 1,1-(3-ethylphenyl)phenylethylene represented by the formula (I) and its manufacturing method, and according to the present invention, Ketoprofen can be synthesized at a low cost and in a high yield.

1 Claim, No Drawings

1,1-(3-ETHYLPHENYL)PHENYLETHYLENE AND METHOD FOR PREPARING IT

BACKGROUND OF THE INVENTION (1) Field of the Invention

The present invention relates to 1,1-(3-ethylphenyl)-phenylethylene represented by the formula (I):

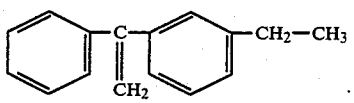

This compound represented by the formula (I) is an intermediate from which α-(3-benzoylphenyl)propionic acid (trade name: Ketoprofen) will be manufactured at a low cost, Ketoprofen being represented by the following formula and being useful as a medicine such as an antiinflammatory agent or an anodyne:

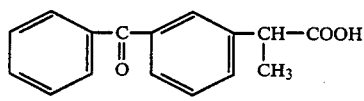

(2) Description of the Prior Art

Heretofore, various manufacturing methods for Ketoprofen have been suggested, and their typical examples are as follows:

(1) The compound 3-methylbenzophenone is bromized to form 3-bromomethylbenzophenone, and the latter is then reacted with potassium cyanide to prepare 3-cyanomethylbenzophenone. The latter is then methylated with methyl iodide in the presence of a base, followed by an alkali hydrolysis, there by obtaining Ketoprofen (Japanese Patent Provisional Publication No. 115452/1976):

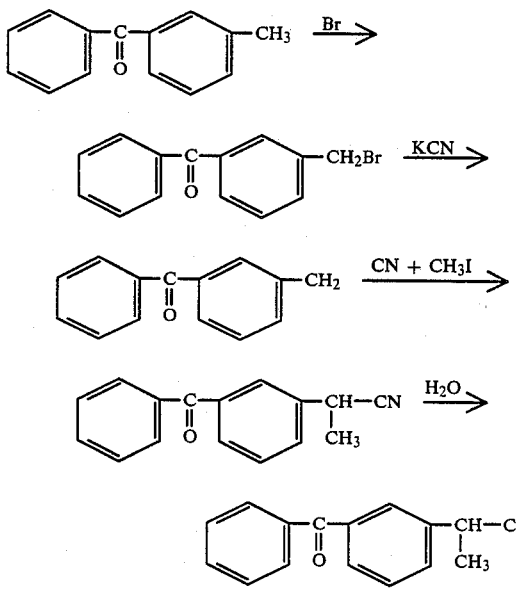

(2) In the presence of a strong base, 3-chlorobenzoic acid is reacted with propionitrile to form (3-carbonylphenyl) propionitrile, and tyonyl chloride is then used to prepare (3-chlorocarbonylphenyl)propionitrile. Afterward, in the present of aluminum chloride, the Friedel-Crafts reaction with benzene is carried out in order to form 3-(1-cyanoethyl)benzophenone, followed by an alkali hydrolysis thereby obtaining Ketoprofen (Japanese Patent Publication No. 8301/1977).

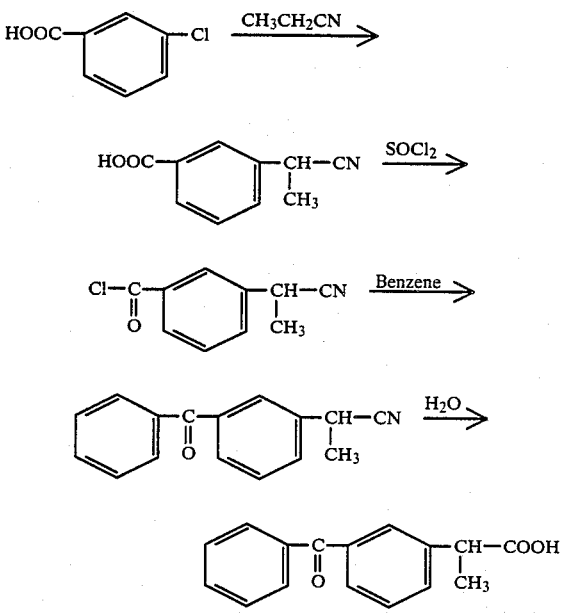

(3) Benzophenone is subjected to the Friedel-Crafts reaction by the use of diethyl sulfate in the presence of aluminum chloride in order to form 3-ethylbenzophenone (II). The latter is then bromized with N-bromosuccinimide to prepare 3-(1-bromoethyl)benzophenone (III), and afterward an alkali hydrolysis is carried out to form 3-(1-hydroxyethyl)benzophenone (IV). Further, the latter is reacted with carbon monoxide, thereby obtaining Ketoprofen (V) (Spanish patent No. 4525000).

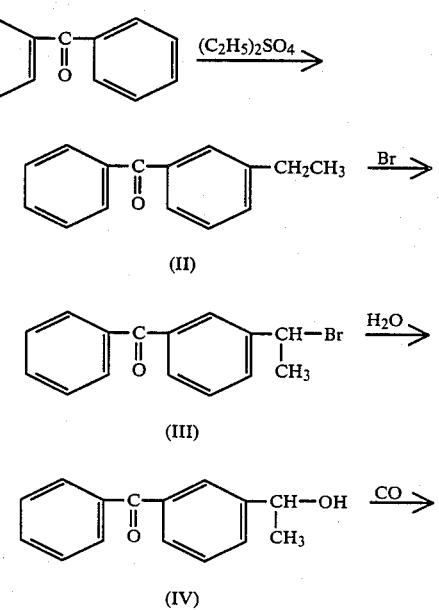

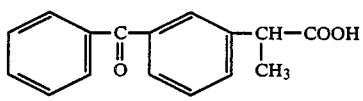

(V)

(4) As a method for manufacturing 1,1-ethylphenyl-phenylethylene, there has been suggested a process of adding phenylacetylene to ethylbenzene by an aralkylation reaction (Neftekhimiya, 14(5), 1974, p. 726–729). However, it is merely confirmed in this reaction that 1,1-(2-ethylphenyl)phenylethylene and 1,1-(4-ethylphenyl)phenylethylene alone are produced which are an o-isomer and a p-isomer. In addition, it is impossible to manufacture Ketoprofen from the o-isomer or the p-isomer as a starting material. Because it is generally difficult to prepare a desired compound by transferring a certain substituent on a position isomer, and such an isomerization reaction is additionally required and has not been elucidated theoretically yet. Incidentally, any example of preparing Ketoprofen from the above mentioned o-isomer or p-isomer has not been known.

The method of the preceding paragraph (1) makes use of poisonous potassium cyanide in the time of synthesizing 3-cyanomethylbenzophenone, and therefore it is not preferred as an industrial manufacturing method. Further, in synthesizing (3-carbonylphenyl)propionitrile by the method in the previous paragraph (2) and 3-ethylbenzophenone by the method in the paragraph (3), the absorptions of their compounds are poor disadvantageously in both the cases. For these reasons, these methods described above are not industrially satisfactory.

SUMMARY OF THE INVENTION

An object of the present invention is to provide a novel intermediate 1,1-(3-ethylphenyl)phenylethylene represented by the formula:

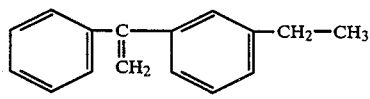

Another object of the present invention is to provide a method for manufacturing 1,1-(3-ethylphenyl)-phenylethylene at a low cost and in a high yield.

DESCRIPTION OF THE PREFERRED EMBODIMENT

The product 1,1-(3-ethylphenyl)phenylethylene having the formula (I) can be synthesized in a high yield, for example, by the following procedure:

The compound m-ethylacetophenone (VI) which is a starting material is reacted with phenylmagnesium bromide which is a Grignard reagent, followed by hydrolysis in order to form 1,1-(3-ethylphenyl)phenylethanol (VII). A temperature for the Grignard reaction is within the range of 10 to 50° C., and the amount of phenylmagnesium bromide is within the range of 1.0 to 1.2 equivalents.

Next, the thus prepared alcohol (VII) is dehydrated in the presence of a dehydrating agent in order to obtain 1,1-(3-ethylphenyl)phenylethylene (I). Usable examples of the dehydrating agents include sulfuric acid, hydrochloric acid, phosphoric acid and potassium hydrogensulfate. A reaction temperature is within the range of 10 to 300° C., and a pressure is ordinary pressure or a reduced pressure at which the reaction makes progress smoothly.

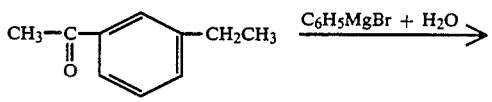

(VI)

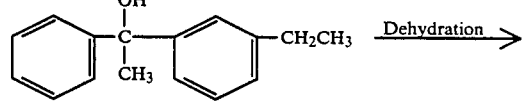

(VII)

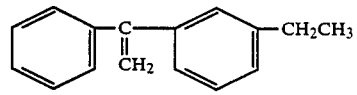

(I)

The product 1,1-(3-ethylphenyl)phenylethylene represented by the formula (I) of the present invention may be oxidized in accordance with a method described in Japanese Patent Provisional Publication No. 32459/1979 to form 3-ethylbenzophenone. This oxidation can be carried out with molecular oxygen by using, as a catalyst, a napthenate of a metal such a cobalt selected from the group VI-b, VII-b or VIII of the periodic table. The amount of the catalyst is suitably within the range of 0.05 to 5% by weight based on the weight of the raw material. The oxidation temperature is from 30° to 250° C., preferably from 90° to 200° C. The pressure is ordinary pressure or a reduced pressure.

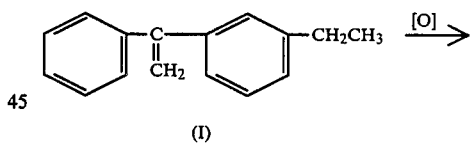

(I)

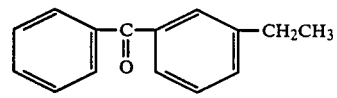

(II)

The compound 3-ethylbenzophenone represented by the formula (II) obtained in the above manner is the starting material of Ketoprofen in the aforesaid Spanish patent No. 452500. Therefore, if the reaction is performed in accordance with this Spanish patent, Ketoprofen can be obtained.

That is, 3-(1-bromoethyl)benzophenone can be formed by reacting 3-ethylbenzophenone with N-bromosuccinimide in the presence of a radical generator such as benzoyl peroxide in a solvent such as carbon tetrachloride, as described above. The thus formed 3-(1-bromoethyl)benzophenone is then heated together with an aqueous, solution of an alkali such as calcium carbonate to hydrolyze it, whereby 3-(1-hydroxyethyl)- benzophenone is prepared. Afterward, the latter is reacted with carbon monoxide with the aid of a noble metal catalyst such as palladium chloride, rhodium chloride and phosphine palladium chloride, thereby obtaining Ketoprofen.

EXAMPLE

Now, the present invention will be described in detail in reference to an example, which does not intend to restrict the scope of the present case.

(1) Synthesis of 1,1-(3-ethylphenyl)phenylethanol (VII)

In a 2 liter flask equipped with a reflux condenser and a stirrer, 50 ml of ether which had been dried with metallic sodium and 28 g (1.15 mols) of metallic magnesium were placed. While stirring the resultant mixture at room temperature, 500 ml of a dry ether solution containg 160 g (1.02 mols) of benzene bromide was gradually added dropwise to the resultant mixture over 2 hours. The reaction temperature was maintained at 35° C. After the completion of the dripping addition, stirring was further continued at 35° C. for 1 hour. Next, 500 ml of a dry ether solution containing 148 g (1.00 mol) of m-ethylacetophenone (VI) was gradually added thereto dropwise over 2 hours, and stirring was further carried out at 35° C. for 1 hour. After the resultant reaction solution had been thrown into an ice water, the separation of solutions was made to recover an ether layer, and the latter was then distilled off under a reduced pressure in order to obtain 1,1-(3-ethylphenyl)-phenylethanol having the formula (VII). This alcohol could be fed to a subsequent process directly without any additional purification, because of dehydrating relatively easily by heating or the like.

(2) Synthesis of 1,1-(3-ethylphenyl)phenylethylene

In a 500 ml three-necked flask equipped with a dropping funnel, 20 g of potassium hydrogensulfate was placed, and was then heated up to 230° to 240° C. under a reduced pressure. Afterward, the alcohol prepared in the preceding paragraph (1) was added thereto dropwise through the dropping funnel. In consequence, the alcohol was dehydrated to an olefin, which was immediately distilled off and was recovered in an outside receiver. From the thus recovered product, water was separated, and vacuum distillation was further carried out in order to form 150 g of 1,1-(3-ethylphenyl)-phenylethylene (I) in a yield of 72%. The analytical results of the product are as follows:

Boiling point: 172 to 174° C./3 mmHg.
IR (Neat)cm$^{-1}$: 3060, 3040, 2960, 1600, 1490, 890, 800, 770, 700.
$^1$H-NMR (CCl$_4$, 6ppm): 6.80 to 7.60 (9H, multiplet); 5.35 (2H, singlet); 2.40 to 2.85 (2H, quartet); 1.05 to 1.40 (3H, triplet).
Elemental analysis (as C$_{16}$H$_{16}$) Calculated values: C=92.31%, H =7.69%. Found values: C =92.33%, H =7.67%.

(3) Synthesis of 3-ethylbenzophenone (II)

In a 50 ml reactor equipped with a stirrer, 20 g of 1,1-(3-ethylphenyl)phenylethylene and 40 mg of cobalt naphthenate were put, and pure oxygen was blown thereinto at a reaction temperature of 110° C. at 50 ml/min for 10 hours. According to the results of gas chromatography and MASS analysis, the conversion of 1,1-(3-ethylphenyl)phenylethylene and the selectivity of 3-ethylbenzophenone were 98.1% and 89%, respectively.

(4) Synthesis of 3-(1-bromoethyl)benzophenone (III)

Into a 200 ml reactor equipped with a reflux condenser and a stirrer, 60 ml of carbon tetrachloride and 10 g of 3-ethylbenzophenone were introduced. While stirring the resultant mixture at room temperature, 8.6 g of N-bromosuccinimide and 0.14 g of benzoyl peroxide were added thereto, and reflux was performed for 8 hours while stirring the reaction solution. After the reaction solution had been cooled to room temperature, the succinimide was filtered out, and carbon tetrachloride was distilled off from a filtrate under a reduced pressure. The spectrum data of the obtained product were in accord with those of 3-(1-bromoethylbenzophenone.

(5) Synthesis of 3-(1-hydroxyethyl)benzophenone (VI)

In an autoclave, 100 ml of water and 3.3 g of calcium carbonate and 10 g of 3-(1-bromoethyl)benzophenone were placed, and were then heated at 120° C. for 6 hours. The resultant reaction solution was extracted with benzene, and a formed benzene layer was then dried with anhydrous sodium sulfate, followed by distilling off the solvent. The resultant product had the spectrum data which were identical with those of 3-(1-hydroxyethyl)benzophenone.

(6) Synthesis of Ketoprofen (V)

In 50 ml of anhydrous ethanol containing 1.5% of hydrogen chloride, 10 g of 3-(1-hydroxyethyl)benzophenone was dissolved, and an anhydrous ethanol solution containing 0.1 g of [P(CH$_3$)$_3$]PdCl$_2$ was then added thereto. This solution was introduced into an autoclave and was then heated at 95° C. at 500 atms for 5 hours in an atmosphere of carbon monoxide. The reaction solution was then transferred to a 200 ml reactor equipped with a reflux condenser and a stirrer, and 5 ml of concentrated hydrochloric acid was added thereto. Afterward, reflux was carried out for 4 hours in a nitrogen atmosphere. Water was then added to the reaction solution, and extraction was performed by the use of ether. The resultant ether layer was washed with water and was then extracted with a 5% aqueous potassium hydroxide solution. After a water layer had been acidified with hydrochloric acid, extraction was performed by the utilization of ether again. The ether layer was then washed with water and dried with anhydrous sodium sulfate, and ether was distilled off under a reduced pressure. The desired α-(3-benzoylphenyl)propionic acid (Ketoprofen) was obtained by its recrystallization from benzene/petroleum ether. Spectra and a melting point of the thus obtained Ketoprofen were the same as those of its authentic sample.

As described in detail above, when 1,1-(3-ethylphenyl)phenylethylene of the present invention which is a novel intermediate is utilized, Ketoprofen can be manufactured via this intermediate with ease in a high yield and at a low cost.

What is claimed is:

1. 1,1-(3-ethylphenyl)phenylethylene represented by the formula (I);

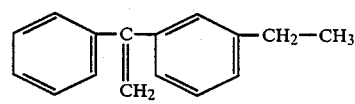

* * * * *